United States Patent [19]

Leong

[11] Patent Number: 5,176,907
[45] Date of Patent: Jan. 5, 1993

[54] BIOCOMPATIBLE AND BIODEGRADABLE POLY (PHOSPHOESTER-URETHANES)

[75] Inventor: Kam W. Leong, Ellicott City, Md.

[73] Assignee: The Johns Hopkins University School of Medicine, Baltimore, Md.

[21] Appl. No.: 744,291

[22] Filed: Aug. 13, 1991

[51] Int. Cl.⁵ .............. A61K 31/74; C08G 18/28; C08G 18/48; C08G 18/10
[52] U.S. Cl. .................. 424/78.08; 424/423; 424/426; 424/430; 424/432; 528/59; 528/66; 528/72; 528/76; 528/85
[58] Field of Search ............ 424/78.08, 423, 426, 424/430, 432; 528/59, 66, 72, 76, 79, 85

[56] References Cited

U.S. PATENT DOCUMENTS 3,153,013  10/1964  Campbell .................. 528/72
4,268,633   5/1981  Fearing et al. ............ 528/72
4,298,709  11/1981  Ginter et al. ............. 528/72

*Primary Examiner*—Thurman K. Page
*Assistant Examiner*—Carlos Azpuru
*Attorney, Agent, or Firm*—John R. Wetherell, Jr.

[57] ABSTRACT

Biocompatible and biodegradable poly(phosphoester-urethanes), compositions comprising the poly(phospho-ester-urethanes), and methods of use as a drug delivery device and an implant.

9 Claims, 4 Drawing Sheets

BIOCOMPATIBLE AND BIODEGRADABLE POLY (PHOSPHOESTER-URETHANES)

BACKGROUND OF THE INVENTION

This invention was in part made with grants awarded by the Whitaker Foundation and the National Institute for Health (EY07701).

FIELD OF THE INVENTION

This invention relates to biocompatible and biodegradable poly-(phosphoesterurethanes) and methods of using these polymers.

DESCRIPTION OF THE BACKGROUND ART

Many polymeric materials have been used as components of devices for diagnosis or therapy, where they have had a significant impact on the clinical success of implant technology. These materials have been used, for example, as orthopedic devices, ventricular shunts, drug-carriers, contact lens', heart valves, sutures, and burn dressings. These polymers can be non-biodegradable or biodegradable.

In traditional drug delivery, it has long been recognized that tablets, capsules, and injections may not be the best mode of administration. These conventional routes often involve frequent and repeated doses, resulting in a "peak and valley" pattern of therapeutic agent concentration. Since each therapeutic agent has a therapeutic range above which it is toxic and below which it is ineffective, a fluctuating therapeutic agent concentration may cause alternating periods of ineffectiveness and toxicity. For this reason, controlled release provides a way of maintaining the therapeutic agent level within the desired therapeutic range for the duration of treatment. Using a polymeric carrier is one effective means to deliver the therapeutic agent locally and in a controlled fashion (Langer, et al., *Rev. Macro. Chem. Phys.*, C23(1), 61, 1983). Such systems require less total drug and, as a result, systemic side effects can be minimized.

Polymers have been used as carriers of therapeutic agents to effect a localized and sustained release (*Controlled Drug Delivery*, Vol. I and II, Bruck, S.D., (ed.), CRC Press, Boca Raton, Fla., 1983; Leong, et al., *Adv. Drug Delivery Review*, 1:199, 1987). These therapeutic agent delivery systems simulate infusion and offer the potential of enhanced therapeutic efficacy and reduced systemic toxicity.

For a non-biodegradable matrix, the steps leading to release of the therapeutic agent are water diffusion into the matrix, dissolution of the therapeutic agent, and out-diffusion of the therapeutic agent through the channels of the matrix. As a consequence, the mean residence time of the therapeutic agent existing in the soluble state is longer for a non-biodegradable matrix than for a biodegradable matrix where a long passage through the channels is no longer required. Since many pharmaceuticals have short half-lives it is likely that the therapeutic agent is decomposed or inactivated inside the non-biodegradable matrix before it can be released. This issue is particularly significant for many bio-macromolecules and smaller polypeptides, since these molecules are generally unstable in buffer and have low permeability through polymers. In fact, in a non-biodegradable matrix, many bio-macromolecules will aggregate and precipitate, clogging the channels necessary for diffusion out of the carrier matrix. This problem is largely alleviated by using a biodegradable matrix which allows controlled release of the therapeutic agent. Biodegradable polymers differ from non-biodegradable polymers in that they are consumed or biodegraded during therapy. This usually involves breakdown of the polymer to its monomeric subunits, which should be biocompatible with the surrounding tissue. The life of a biodegradable polymer in vivo depends on its molecular weight and degree of cross-linking; the greater the molecular weight and degree of crosslinking, the longer the life. The most highly investigated biodegradable polymers are polylactic acid (PLA), polyglycolic acid (PGA), polyglycolic acid (PGA), copolymers of PLA and PGA, polyamides, and copolymers of polyamides and polyesters. PLA, sometimes referred to as polylactide, undergoes hydrolytic de-esterification to lactic acid, a normal product of muscle metabolism. PGA is chemically related to PLA and is commonly used for absorbable surgical sutures, as is the PLA/PGA copolymer. However, the use of PGA in controlled-release implants has been limited due to its low solubility in common solvents and subsequent difficulty in fabrication of devices.

An advantage of a biodegradable material is the elimination of the need for surgical removal after it has fulfilled its mission. The appeal of such a material is more than simply for convenience. From a technical standpoint, a material which biodegrades gradually and is excreted over time can offer many unique advantages.

A biodegradable therapeutic agent delivery system has several additional advantages: 1) the therapeutic agent release rate is amenable to control through variation of the matrix composition; 2) implantation can be done at sites difficult or impossible for retrieval; 3) delivery of unstable therapeutic agents is more practical. This last point is of particular importance in light of the advances in molecular biology and genetic engineering which have lead to the commercial availability of many potent bio-macromolecules. The short in vivo half-lives and low GI tract absorption of these polypeptides render them totally unsuitable for conventional oral or intravenous administration. Also, because these substances are often unstable in buffer, such polypeptides cannot be effectively delivered by pumping devices.

In its simplest form, a biodegradable therapeutic agent delivery system consist of a dispersion of the drug solutes in a polymer matrix. The therapeutic agent is released as the polymeric matrix decomposes, or biodegrades into soluble products which are excreted from the body. Several classes of synthetic polymers, including polyesters (Pitt, et al., in *Controlled Release of Bioactive Materials*, R. Baker, Ed., Academic Press, New York, 1980); polyamides (Sidman, et al., *Journal of Membrane Science*, 7:227, 1979); polyurethanes (Maser, et al., *Journal of Polymer Science, Polymer Symposium*, 66:259, 1979); polyorthoesters (Heller, et al., *Polymer Engineering Science*, 21:727, 1981); and polyanhydrides (Leong, et al., *Biomaterials*, 7:364, 1986) have been studied for this purpose.

All prior art biodegradable polymers possess some degree of imperfection such as weak mechanical strength, unfavorable degradation characteristics, toxicity, inflexibility, or fabrication difficulty. Although these biodegradable polymers have a broad range of potential utility, there is no one single material available that could satisfy all requirements imposed by different applications. Accordingly, there is a definite need to develop new biodegradable polymers.

The biodegradable matrix of the invention finds broad utility as a transient prosthetic support in orthopedic applications. For centuries, physicians have attempted to repair and replace various components of the skeletal system. These attempts have utilized various kinds of materials including bone, ivory, collagen, wood, metals, alloys, ceramics, glasses, corals, carbons, polymers, and composites of materials as bone prostheses.

Ideally, the bone prosthesis should be a material that is biologically inert, readily available, easily adaptable to the site in terms of shape and size, and replaceable by the host bone. Replacement of the prothesis by the host bone necessitates that the substitute be biodegradable.

The different elastic moduli of the prior art prosthetic implants versus that of bone often causes cortical bone to atrophy. The theoretical advantage of gradual load transfer from the bone plate to the bone and the elimination of the need for surgical removal after the healing of a fracture would make an absorbable osteosynthetic material extremely useful. As a temporary support in a load-bearing area of an articular joint, a resorbable porous material also has the advantage of preventing further destruction of cartilage defects and promoting bone and cartilage-forming cells. Hence, a need exists for a biodegradable prosthesis of sufficient post-implantation strength and rigidity to provide structural support.

European Patent Application 0386,757 (published Dec. 9, 1990), which is hereby incorporated by reference, discloses a new class of poly(phosphate esters). These polymers are biocompatible and biodegradable, and find application as prostheses, drug delivery devices, and other biomedical materials.

Polyurethanes, because of their excellent mechanical strength and good blood and tissue compatibility, have been used in a number of prosthetic devices. Biodegradable polyurethanes have also attracted considerable interest, as described in Bruin P., et al., *Biomaterials*, 11:291, 1990. While such biodegradable polymers have promise for use in a controlled drug delivery device, these prior art polymers have been of limited usefulness because of their slow degradation rate. Consequently, the need for new polyurethane materials which can be used to fabricate prostheses or drug delivery devices continues to exist.

SUMMARY OF THE INVENTION

This invention pertains to a biocompatible and biodegradable poly(phosphoester urethane) useful as a structural prosthesis and a therapeutic agent delivery vehicle as well as to methods for its manufacture and use. This invention also relates to a composition which comprises a biocompatible and biodegradable poly(phosphoester urethane) matrix, prepared in preselected dimensions and configurations, which predictably degrades in vivo into small molecules. The method of using the composition as an implant and prosthesis comprises the step of introducing a specifically configured composition into an individual in vivo at a predetermined site.

The composition of the invention, through its transient in vivo presence, provides a matrix which persists for a period of time sufficient to achieve a medical effect, essentially lacks host toxicity upon degradation, provides mechanical strength, and is readily fabricated.

Various aspects of this invention are practiced by the use of a biocompatible and biodegradable poly-(phosphoester-urethane) of the formula:

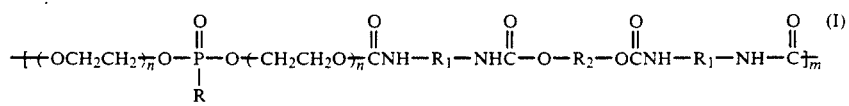

wherein R is hydrogen, alkyl having $C_1$-$C_{12}$, or a residue of a therapeutic agent capable of being released in a physiological environment;

$R_1$ is selected from the group consisting of $C_2$-$C_{20}$ alkylene, $C_6$-$C_{20}$ arylene, $C_7$-$C_{20}$ aralkylene, $C_6$-$C_{20}$ cycloalkylene, and a divalent residue of an amino acid, an amino acid derivative or an amino acid mimetic;

$R_2$ is selected from the group consisting of $C_2$-$C_6$ polyalkylene having a molecular weight of from about 500 to about 2000, $C_2$-$C_6$ polyalkenylene having a molecular weight of from about 500 to about 2000, $C_7$-$C_{20}$ aralkylene, $(R_3O)_l$ wherein $R_3$ is $C_2$-$C_6$ alkylene or acyl having from 2 to 6 carbons, and $l$ is an integer of from 5 to 30, and

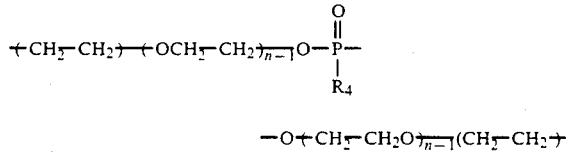

wherein $R_4$ is hydrogen or alkyl having $C_1$-$C_{12}$;
n is an integer of from 2 to 6; and
m is an integer of from about 10 to about $10^5$.

DETAILED DESCRIPTION

Figure 1:
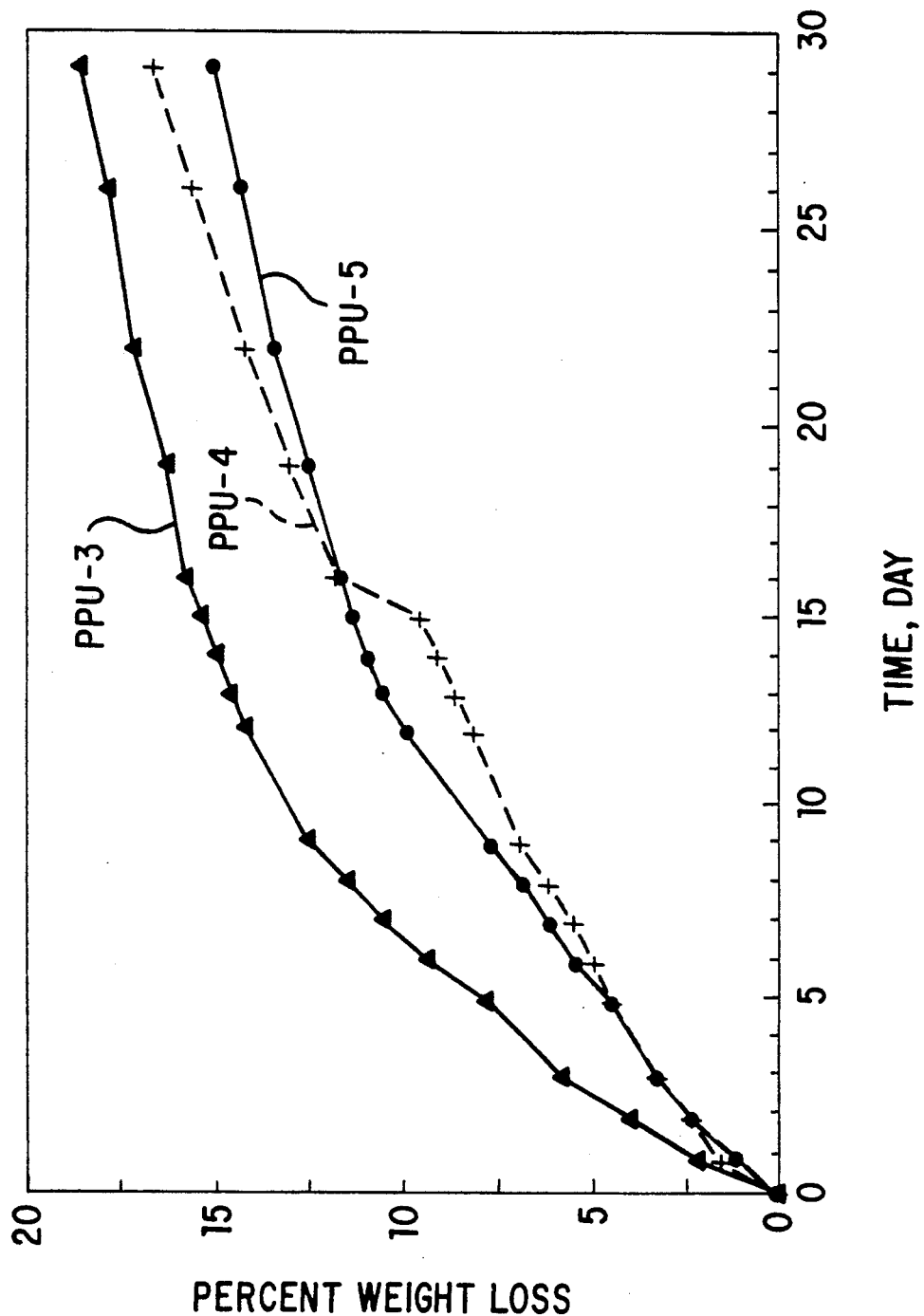
FIG. 1 compares the time-dependant degradation (as expressed in terms of mass loss) of various poly(phosphoester-urethanes) according to this invention.

This invention is directed to poly(phosphoester-urethanes) useful as prostheses and as therapeutic agent delivery vehicles and devices. The polymers are biodegradable because of the hydrolyzable phosphoester, or $P(O)$—$O$—$C$ bond, in the backbone.

In accordance with a process employed for the preparation of the instant polymers, a prepolymer of formula (II) is first formed by reacting a diisocyanate of formula (III) and a diol of formula (IV) as set forth below.

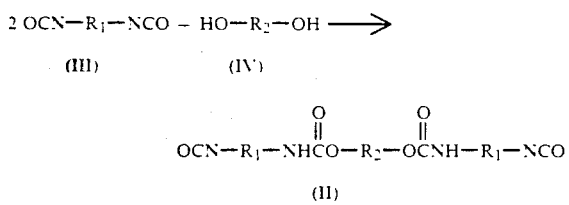

(II)

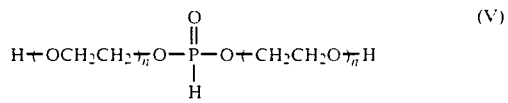

wherein n is an integer of from 2 to 6, preferably 2.

Condensation is carried out substantially under the same conditions as those used for the preparation of the prepolymer (II) until a degree of condensation (m) of from about 10 to about $10^5$ is achieved. Typically, the condensation is terminated by quenching with water within a few hours.

In the above formulae (II), (III), and (IV), $R_1$ and $R_2$ are each as defined previously. The diol (IV) is condensed with substantially two equivalents of the diisocyanate (III). This and the subsequent condensations are normally carried out in a reaction-inert solvent in which both the reactants are miscible. Preferred organic solvents for use in condensation include N,N-dimethylacetamide, N,N-dimethylformamide, dimethylsulfoxide, and tetrahydrofuran. The temperature of condensation is preferably from about 60° to about 120° C., preferably from about 100° to about 110° C.

When $R_1$ is $C_2$–$C_{20}$ alkylene, the diisocyanate (III) is preferably 2,2,4-trimethylhexamethylene diisocyanate. When $R_1$ is $C_6$–$C_{20}$ arylene, the diisocyanate (III) is preferably 1,5-naphthalene diisocyanate. When $R_1$ is $C_6$–$C_{20}$ cycloalkylene, the diisocyanate (III) is preferably selected from 1,6-hexane diisocyanate, methylene bis(p-cyclohexyl isocyanate), and isophorone diisocyanate. When $R_1$ is $C_7$–$C_{20}$ aralkylene, the diisocyanate (III) is preferably selected from 2,4-toluene diisocyanate (2,4 TDI), 2,6-toluene diisocyanate (2,6 TDI), methylene bis-(P-phenylisocyanate) (MDI, also known as 4,4'-diphenylmethane diisocyanate), and 3,3'-bitoluene diisocyanate.

When $R_1$ is a divalent residue of an amino acid, an amino acid derivative or an amino acid mimetic which provides two terminal amino groups, the diisocyanate (III) is preferably derived from basic amino acids such as lysine, hydroxyllysine, and arginine. Alkyl 2,6-diisocyanatohexanoate (e.g., ethyl 2,6-diisocyanatohexanoate; LDI), which is obtainable from L-lysine, is particularly preferred.

When $R_2$ is $C_2$–$C_6$ polyalkylene having a molecular weight of from about 500 to 2000, $R_2$ is preferably polyisobutylene. When $R_2$ is $C_2$–$C_6$ polyalkenylene having a molecular weight of from about 500 to 2000, $R_2$ is preferably 1,4-polybutadiene. When $R_2$ is $(R_3O)_f$, wherein $R_3$ is $C_2$–$C_6$ alkylene, the diol (IV) is preferably selected from poly-(ethylene glycol) [or PEG], poly-(propylene-1,2-glycol), poly-(propylene-1,3-glycol), poly-(tetramethylene-1,4-glycol), poly-(pentamethylene-1,5-glycol), and poly-(hexamethylene-1,6-glycol). Within this group of diols, the molecular weight of the diols is preferably from about 500 to about 1000. Especially preferred individual diols are poly-(ethylene glycol) and poly-(tetramethylene-1,4-glycol). When $R_2$ is $(R_3O)_f$, wherein $R_3$ is acyl having from 2 to 6 carbons, the diol (IV) is preferably poly(caprolactonediol). When $R_2$ is $C_7$–$C_{20}$ aralkylene, the diol (IV) is preferably selected from bisphenol-A (4,4'-isopropylidene diphenol) and 1,4-benzene dimethanol.

The thus-formed prepolymer (II) is then condensed with a substantially equivalent portion of a chain extender of formula (V).

The novel poly-(phosphoester-urethane) of formula (I) wherein R is hydrogen, can thus be obtained and also isolated in a standard manner (e.g., filtration followed by washing with deionized water, and drying).

In an alternative version of the polymerization, the poly-(phosphoester-urethanes) may be prepared by simultaneously mixing together the diisocyanate (III), the diol (IV), and the chain extender (V).

The poly-(phosphoester-urethanes) (I) are readily converted to implantable biomedical devices by established techniques such as extrusion, injection molding, and dip casting.

In one aspect of the invention, an alkyl having $C_1$–$C_{12}$ can be attached to the polymer backbone at the phosphorous atom of the polymer (I) according to standard methods known in the art. See, Penczek, et al., *Pure & Applied Chem.*, 56:1309, 1984.

In a particular aspect of the invention, a therapeutic agent is introduced into the poly-(phosphoester-urethane) (I) wherein R is hydrogen, by covalently binding a radical of the therapeutic agent to the phosphorous atom of the polymer (I).

A typical reaction using 5-fluorouracil (5-FU) is illustrated as follows:

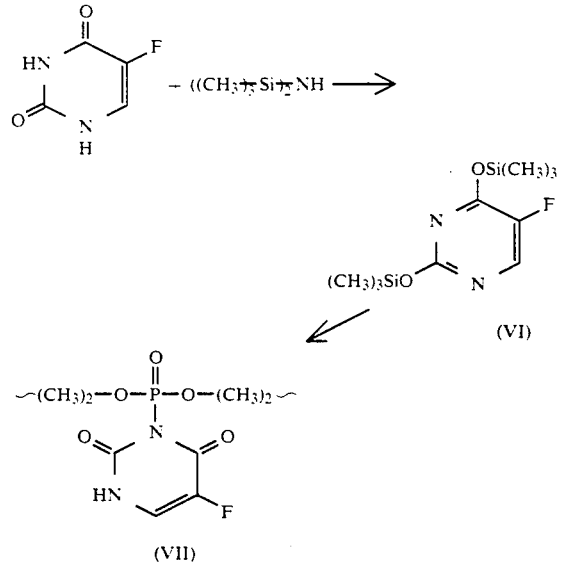

The above reaction involves silyl enolization of the 2,4-keto positions of 5-FU, followed by desilylation to render the 3 nitrogen atom of 5-FU attached to the phosphorous atom of the polymer (I). The coupling of the 5-FU molecule is typically carried out in dichloromethane by combining the polymer (I), wherein R is hydrogen, and a disilylated 5-FU of formula (VI) in the presence of triethylamine at ambient temperature for about 48 hours. The resultant polymer of formula (VII) can be isolated by conventional means (e.g., precipitation).

It will be realized that the above sequence is merely illustrative of a method adapted for use with a particular therapeutic agent, and that any therapeutic agent bearing a suitable reactive site can be chemically appended to the phosphorous atom of the polymer (I) according to standard techniques known in medicinal chemistry.

The term "therapeutic agent" used herein includes, without limitation, drugs, radioisotopes, immunomodulators, and lectins. Similar substances are within the skill of the art. The term "individual" includes human as well as non-human animals.

The drugs which can be employed in the invention include non-proteinaceous as well as proteinaceous drugs. The term "non-proteinaceous drugs" encompasses compounds which are classically referred to as drugs such as, for example, 5-FU, mitomycin C, daunorubicin, vinblastine, AZT, and hormones. Similar substances are within the skill of the art. Such substances include, but are not restricted to analgesics, anorexics, anthelmintics, antibacterials, anticonvulsants, antifungals, antidepressants, antibiotics, antihistamines, antiulcer drugs, antihypertensives, bronchodilators, immunosuppressants, antiinflammatories and blood glucose lowering agents.

The proteinaceous drugs which can be employed in the invention include immunomodulators and other biological response modifiers. The term "biological response modifiers" is meant to encompass substances which are involved in modifying the immune response in such manner as to enhance the particular desired therapeutic effect, for example, the destruction of tumor cells. Examples of immune response modifiers include such compounds as lymphokines. Examples of lymphokines include tumor necrosis factor, interleukins, lymphotoxin, macrophage activating factor, migration inhibition factor, colony stimulating factor and interferons. The interferons which can be used include alpha-interferon, beta-interferon, and gamma-interferon and their subtypes. In addition, peptide or polysaccharide fragments derived from these proteinaceous drugs, or independently, can also be incorporated. Also, encompassed by the term "biological response modifiers" are substances generally referred to as vaccines wherein a foreign substance, usually a pathogenic organism or some fraction thereof, is used to modify the host immune response with respect to the pathogen to which the vaccine relates. Those of skill in the art will know, or can readily ascertain, other substances which can act as proteinaceous drugs.

In using radioisotopes certain isotopes may be more preferable than others depending on such factors, for example, as tumor distribution and mass as well as isotope stability and emission. Depending on the type of malignancy present some emitters may be preferable to others. In general, alpha and beta particle-emitting radioisotopes are preferred in immunotherapy. For example, if an animal has solid tumor foci a high energy beta emitter capable of penetrating several millimeters of tissue, such as $^{90}Y$, may be preferable. On the other hand, if the malignancy consists of single target cells, as in the case of leukemia, a short range, high energy alpha emitter such as $^{212}Bi$ may be preferred. Examples of radioisotopes which can be incorporated in the compositions of the invention for therapeutic purposes are $^{125}I$, $^{131}I$, $^{90}Y$, $^{67}Cu$, $^{212}Bi$, $^{211}At$, $^{212}Pb$, $^{47}Sc$, $^{109}Pd$ and $^{188}Re$. Other radioisotopes which can be incorporated into the compositions of the invention are within the skill in the art.

Lectins are proteins, usually isolated from plant material, which bind to specific sugar moieties. Many lectins are also able to agglutinate cells and stimulate lymphocytes. Other therapeutic agents which can be used therapeutically with the biodegradable compositions of the invention are known, or can be easily ascertained, by those of ordinary skill in the art.

The term "therapeutically effective" as it pertains to the compositions of this invention means that the therapeutic agent is present at concentrations sufficient to achieve a particular medical effect for which the therapeutic agent is intended. Examples, without limitation, of desirable medical effects which can be attained are chemotherapy, antibiotic therapy, birth control, and regulation of metabolism.

"Therapeutic-agent bearing" as it applies to the compositions of this invention denotes that the composition incorporates a therapeutic agent which is 1) not bound to the polymeric matrix, or 2) pendently bound to the polymeric matrix. When the therapeutic agent is not bound to the matrix, then it is merely physically dispersed with the polymer matrix. When the therapeutic agent is pendently attached, it is chemically linked, for example, by ionic or covalent bonding, to the phosphorous atom of the polymer backbone. The therapeutic agent is released as the matrix biodegrades. The drug can also be released by diffusion through the polymeric matrix. In the pendant system, the drug is released as the polymer-drug bond is cleaved at the bodily tissue.

The concentration of therapeutic agent in the composition will vary with the nature of the agent and its physiological role and desired therapeutic effect. Thus, for example, the concentration of a hormone used in providing birth control as a therapeutic effect will likely be different from the concentration of an anti-tumor drug in which the therapeutic effect is to ameliorate a cell-proliferative disease. In any event, the desired concentration in a particular instance for a particular therapeutic agent is readily ascertainable by one of skill in the art.

The therapeutic agent loading level for a composition of the invention can vary, for example, on whether the therapeutic agent is pendently bound to the poly(phosphoester-urethane). For those compositions in which the therapeutic agent is not bound to the backbone matrix, in which the agent is physically dispersed with the poly(phosphoester-urethane), the concentration of agent will typically not exceed 50 wt %. For compositions in which the therapeutic agent is pendently bound to the polymeric matrix, the drug loading level is up to the stoichiometric ratio of agent per monomeric unit.

The poly-(phosphoester-urethane) of this invention show favorable mechanical strength because of the high molecular weights obtainable. The molecular weight of the polymer is not critical. However, the molecular weight can preferably range from about 2,000 to about $10^6$, containing from about 10 to about 100,000 monomeric units. Higher molecular weight leads to transparency, and film and fiber properties. It has also been observed that the P—O—C group provides a plasticizing effect, which lowers the glass transition temperature of the polymer and confers solubility in organic solvents. Both effects are desirable for fabrication of the instant composition.

The term "transient structural prosthesis" when used to describe the compositions of this invention means a prosthesis which is biodegradable with time and provides a structural function and support in a subject receiving implantation such as, for example, as a vascular graft, suture and bone plate.

A poly(phosphoester-urethane) composition of the invention can function simultaneously both as a transient structural prosthesis and as a therapeutic agent-bearing composition. An example of this would be a suture bearing a therapeutic agent such as, for example, an antibiotic, or, alternatively, a bone plate incorporating a growth factor.

A novel advantage of the polymers of the invention is the availability of a bonding site which allows the chemical linkage of therapeutic agents to the polymer backbone. For example, drugs with carboxyl groups can be coupled to the phosphorous atom via an ester bond, which itself is hydrolyzable. The rate of therapeutic agent release will then be dependent on the hydrolytic cleavage of the polymer therapeutic agent conjugate. This pendant delivery system has the advantage of attaining a high drug loading level. Therapeutic agents which exist in the liquid state can also be accommodated.

All of the compositions useful as prostheses or implants are synthetic poly(phosphoester-urethane) compositions which share such characteristics as predictable and controllable degradation rates, biocompatibility and biodegradability, mechanical strength, and ease of fabrication.

The rate of biodegradation of the poly(phosphoester-urethane) compositions of the invention may also be controlled by varying the hydrophobicity of the polymer.

The mechanism of predictable degradation preferably relies on either group $R_1$ and $R_2$ in the polymer backbone being hydrophobic, for example, an aromatic structure, or, alternatively, if the group $R_1$ is not hydrophobic, for example, an aliphatic group, then the group $R_2$ is preferably aromatic.

The rates of degradation for each poly(phosphoester-urethane) composition are generally predictable and constant at a single pH. This permits the compositions to be introduced to the individual at a variety of tissue sites. This is especially valuable in that a wide variety of compositions and devices to meet different, but specific, applications may be composed and configured to meet specific demands, dimensions, and shapes—each of which offers individual, but different, predictable periods for degradation.

Biodegradation of the poly(phosphoester-urethanes) produces a segment with one end terminated by amine. The biodegradated segment may further break down to a diamine of the formula $H_2N—R_1—NH_2$. Where an aromatic diisocyanate (I) such as methylenediphenyl diisocyanate is used, the suspected toxic, carcinogenic methylenedianiline may be released in vivo. On the other hand, amino acid-derived diisocyanetes degrades in vivo to release non-toxic degradation products. For this reason, in the practice of this invention, the diisocyanetes (III) where $R_1$ is derived from L-lysine is particularly preferred compared to those wherein $R_1$ is $C_6$-$C_{20}$ arylene.

When the composition of the invention is used for long term delivery of a therapeutic agent, a relatively hydrophobic backbone matrix, for example, containing bisphenol A, is preferred. It is possible to enhance the degradation rate of the poly(phosphoester-urethane) or shorten the functional life of the device, by introducing hydrophilic or polar groups, into the backbone matrix. Further, the introduction of methylene groups into the backbone matrix will usually increase the flexibility of the backbone and decrease the crystallinity of the polymer. Conversely, to obtain a more rigid backbone matrix, for example, when used orthopedically, an aromatic structure, such as a diphenyl group, can be incorporated into the matrix. Also, the poly(phosphoester-urethanes) can be crosslinked, for example, using 1,3,5-trihydroxybenzene or $(CH_2OH)_4C$, to enhance the modulus of the polymer.

The entire class of poly(phosphoester-urethane) are biocompatible and biodegradable. In view of their intended function as a therapeutic agent-bearing implant or prosthesis to be introduced into a subject in vivo, it is desirable that these compositions be essentially non-inflammatory, and non-immunogenic.

The use of the poly(phosphoester-urethane) of this invention as an implant which also functions as a therapeutic agent-bearing polymeric composition, for example, subcutaneously or in various body cavities, is particularly useful in cases where chronic administration of drug over periods ranging from days to years is required. Examples of drugs which can be used in this manner include insulin for diabetes, pilocarpine for glaucoma, immune agents for various diseases and allergies, contraceptive steroids, narcotic antagonists, antibiotics, anticancer, and antihypertensive drugs.

Subcutaneous implantation is currently one of the most popular routes used for sustained drug delivery. This is partly due to the simplicity of the surgical procedures involved in implantation and removal, and the relatively favorable absorption site offered compared to the oral or percutaneous routes. Surgery could be viewed as a disadvantage, however, depending on the patient and the location and frequency of implantation. It can be avoided in some cases by injecting the implant directly into subcutaneous tissue, provided the implant is capable of being delivered through a syringe. This is the method used for many of the sustained-release insulin products.

Implantation using a syringe is particularly effective when the composition of the invention is in the form of microspheres which can be suspended in a pharmaceutical buffer and introduced via the syringe to the desired site.

For example, compositions in the form of microspheres incorporating cortisone could be injected into the region of an inflammatory joint or muscle.

The use of the biodegradable polymers of this invention to act as a matrix for the release of a therapeutic agent from subcutaneously implanted compositions offers several advantages over prior art compositions. The most obvious is that no surgical removal of the device is necessary after it has fulfilled its function. Also, an additional mechanism for release of drug is provided by degradation. Complete delivery and, thus, maximal absorption occurs after the device has degraded.

Biodegradable subcutaneous implants can also be used, for example, for the delivery of narcotic antagonists, steroids, and anticancer agents. Narcotic antagonists, such as naltrexone, cyclazocine, and naloxone, are therapeutically useful in the postdetoxification stage of rehabilitation of drug-dependent patients. Steroids which can be used include contraceptives (for example, progesterone), anti-inflammatory agents (for example, dexamethasone), and anabolics (for example, estradiol). Anticancer agents which can be used include 5-FU, cyclophosphamide, doxorubicin, and cisplatin.

Intravaginal implants are used for the sustained released of contraceptive steroid hormones due to the more favorable site of absorption offered by the vaginal mucosa relative to the oral route for these drugs. Firstpass hepatic metabolism, which inactivates many steroid hormones, and gastrointestinal incompatibility are avoided by using the vaginal route. In addition, the vaginal route allows self-insertion ensuring better patient compliance. More stable poly(phosphoesterurethane) are preferred in this usage.

The intrauterine device (IUD) is one of the more popular methods of contraception which can utilize the compositions of the invention. Initial investigations involving nonmedicated IUDs revealed that the larger the device, the more effective it was in preventing pregnancy. Unfortunately, large devices caused increased incidences of uterine cramps, bleeding, and expulsion. The effort to improve intrauterine contraception and avoid previously demonstrated side effects has led to the development of medicated IUDs. More stable poly(phosphoester-urethane) are preferred in this usage. Two classes of agents have been used in IUDs of this type: contraceptive metals, such as copper, and steroid hormones, such as progesterone.

The compositions of this invention are also useful in the treatment of glaucoma. Chronic open-angle glaucoma usually requires therapy for the lifetime of the patient with a miotic agent such as pilocarpine, for control of intraocular pressure. Conventional pilocarpine therapy requires installation of eyedrops four times a day.

Hence, compositions of the invention incorporating an anti-glaucoma agent such as pilocorpine would require less frequent and more sustained administration.

The compositions of the invention, when the therapeutic agent is dispersed in the polymer matrix, may contain pharmaceutically acceptable excipients selected with regard to standard pharmaceutical practice. Excipients typically used for this purpose include lactose, sucrose, calcium lactate, magnesium stearate, ethyl cellulose and ethylene vinyl acetate copolymer.

In addition to the embodiments described above, compositions comprising the poly(phosphoester-urethane) of the invention can be used for agricultural purposes. This can be accomplished by substituting for the therapeutic agent, without limitation, a pesticide, a plant growth hormone, a fungicide, a fertilizer, and the like, others of which are known or readily ascertainable to those of skill in the art.

The above disclosure generally describes the present invention. A further understanding can be obtained by reference to the following specific examples which are provided herein for purposes of illustration only, and are not intended to be limiting unless otherwise specified.

EXAMPLE 1

GENERAL POLYMER SYNTHESIS PROCEDURES

Chemicals were purchased from Aldrich chemical company as received unless otherwise noted: 1,1,1,3,3,3-hexamethyl disilazane, ethylene glycol, triphosgene, poly(ethylene oxide) (MW=600), poly(tetramethylene oxide) (MW=1000), poly(caprolatonediol) (MW=530), toluene diisocyanate (TDI), anhydrous ethanol (Barker Analyzed), L-lysine monohydride (Sigma) and methylene bis-4-phenyl isocyanate (MDI) (Kodak). Ethyl ether (Barker Analyzer), triethylamine and Dimethyl acetamide were respectively dried with sodium, calcium hydride and barium oxide overnight, and then distilled. Thionyl chloride and diethylphosphite were distilled before use. Bis(2-hydroxyethyl)phosphate (BEP) and ethyl 2,6-diisocyanatohexanoate (LDI) were prepared according to PREPARATIONS 1 and 2, respectively.

Chemical structure of monomers and intermediates was confirmed by FT-IR (Perkin Elmer 1600) and FT-NMR (Varian XL400). Molecular weight distribution of polymers was assessed by gel permeation chromatograph (GPC) and intrinsic viscosity.

The GPC was performed in a Hewlett-Packard 1090M system equipped with a diode array and a refractive index refractometer. Samples were eluted through three PL-Gel columns in series at 40° C. Polystyrene standards were used to calibrate the system. The intrinsic viscosity measurements were done in Fenske viscometers in DMF at 30° C. The thermal properties of the polymers were analyzed by DSC on a Mettler TA3000 system at a heating rate of 10° C./minute under nitrogen after thermal history of the samples was erased in preliminary heating cycles.

Into a 1000 ml round bottom flask constantly purged by nitrogen were added 200 ml of dried demethylacetamide and 11.5 g of poly(ethylene glycol) (PEG) with a molecular weight of approximately 400. The PEG was predried at 60° C. at a vacuum oven (3 mm Hg) for 24 hours. Fourteen grams of freshly distilled 4,4'-diphenylmethane diisocyanate was then added to the solution which was agitated by a magnetic stirrer. The solution was heated to 100° C. in 30 minutes and allowed to react for 2 hours. After a brief cooling at room temperature, a solution of 4.9 g of freshly prepared bis(2-hydroxyethyl)phosphite in 20 ml of dimethylacetamide was quickly added to the stirred viscous prepolymer solution. The reaction mixture was then heated to 120° C. and allowed to react for 3 hours, again under agitation and nitrogen purge. At the end of the reaction, the mixture was cooled to room temperature and quenched slowly into 1500 ml of rigorously agitated ice cold distilled water over a period of 15 minutes. The product in the form of the white powder was filtered and washed further with 1000 ml of cold distilled water. The polymer was air dried for 24 hours and then vacuum dried for 48 hours at 60° C. and 3 mm Hg. The polymer was stored in a desiccator.

EXAMPLE 2

The reaction and isolation procedures of Example 1 were repeated with the following reactants and amounts:

10 g(0.056 mole)TDI, 11.5 g(0.028 mole)PEG in initial condensation reaction at 100° C.; 4.9 g(0.028 mole)-BEP in second condensatin reaction at 120° C. The polymer so produced was obtained in 80% yield and had an intrinsic viscosity of 1.10 dl/g(in chloroform at 30° C.). The polymer was coded as PPU-2.

EXAMPLE 3

The reaction and isolation procedures of Example 1 were repeated with the following reactants and amounts:

10 g(0.056 mole)TDI, 4.9 g(0.028 mole)BEP in initial condensation reaction at 100° C.; 4.9 g(0.028 mole)BEP in second condensation reaction at 120° C. The polymer so produced was obtained in 90% yield and had viscosity similar to that of the polymer of Example 1. The polymer was coded as PPU-1.

EXAMPLE 4

The reaction and isolation procedures of Example 1 were repeated with the following reactants and amounts:

10 g(0.056 mole)TDI, 6.6 g(0.028 mole)bisphenol-A in initial condensation reaction at 100° C.; 4.9 g(0.028 mole)BEP in second condensation reaction at 120° C. The polymer so produced was obtained in 80% yield and had an intrinsic viscosity of 0.92 dl/g(in chloroform at 30° C.). The polymer was coded as PPU-3.

EXAMPLE 5

The reaction and isolation procedures of Example 1 were repeated with the following reactants and amounts:

10 g(0.056 mole)TDI, 2.45 g(0.014 mole)PEG, 3.3 g (0.014 mole) bisphenol-A in initial condensation reaction at 100° C.; 4.9 g(0.028 mole)BEP in second condensation reaction at 120° C. The polymer so produced had an intrisic viscosity of 0.50 dl/g (in chloroform at 30° C.). The polymer was coded as PPU-4.

EXAMPLE 6

The reaction and isolation procedures of Example 1 were repeated with the following reactants and amounts:

10 g(0.056 mole)TDI, 28.7 g(0.028 mole)poly(tetramethyle-1,4-glycol) in initial condensation reaction at 100° C.; 4.9 g(0.028 mole)BEP in second condensation reaction at 120° C. The polymer so produced was obtained in 90% yield and had an intrinsic viscosity of 1.95 dl/g (in chloroform at 30° C.). The polymer was coded as PPU-6.

EXAMPLE 7

The reaction and isolation procedures of Example 1 were repeated with the following reactants and amounts:

14.4 g(0.056 mole)MDI, 2.45 g(0.014 mole)BEP, 5.75 (0.014 mole)PEG in initial condensation reaction at 100° C.; 4.9 g(0.028 mole)BEP in second condensation reaction at 120° C. The polymer so produced was obtained in 75% yield and had viscosity similar to that of the polymer of Example 1. The polymer was coded as PPU-7.

EXAMPLE 8

The reaction and isolation procedures of Example 1 were repeated with the following reactants and amounts:

14.4 g(0.056 mole)MDI, 4.9 g(0.028 mole)BEP in initial condensation reaction at 100° C.; 4.9 g(0.028 mole)BEP in second condensation reaction at 120° C. The polymer so produced was obtained in 85% yield and had viscosity similar to that of the polymer of Example 1. The polymer was coded as PPU-8.

EXAMPLE 9

The reaction and isolation procedures of Example 1 were repeated with the following reactants and amounts:

13 g(0.056 mole)LDI, 11.5 g(0.028 mole)PEG in initial condensation reaction at 100° C.; 2.45 g(0.014 mole)BEP, 1.98 g(0.014 mole)1.4-benzenedimethanol in second condensation reaction at 120° C. The polymer so produced had a Mw of $6.38 \times 10^6$ and an intrinsic viscosity of 1.25 dl/g (in chloroform at 30° C.). The polymer was coded as PLU-1.

EXAMPLE 10

The reaction and isolation procedures of Example 1 were repeated with the following reactants and amounts:

13 g(0.056 mole)LDI, 40 g(0.028 mole)polycaprolactonediol in initial condensation reaction at 100° C.; 2.45 g(0.014 mole)BEP, 1.98 g(0.014 mole)1.4-benzenedimethanol in second condensation reaction at 120° C. The polymer so produced had a Mw of $7.4 \times 10^6$. The polymer was coded as PLU-2.

EXAMPLE 11

The reaction and isolation procedures of Example 1 were repeated with the following reactants and amounts:

13 g(0.056 mole)LDI, 28.7 g(0.028 mole)PTMO in initial condensation reaction at 100° C.; 2.45 g(0.014 mole)BEP, 1.98 g(0.014 mole)1,4-benzenedimethanol in second condensation reaction at 120° C. The polymer so produced had a Mw of $6.6 \times 10^6$. The polymer was coded as PLU-5.

EXAMPLE 12

PREPARATION OF PENDANT 5-FLUOROURACIL POLYMER

A mixture of 5-FU (7 g) and 1,1,1,3,3,3-hexamethyldisilazane (30 ml) were heated at reflux temperature for 20 hours in the presence of a catalytic amount of ammonium sulphate to derivatize 5-FU. Evaporation of the mixture under reduced pressure resulted in the formation of 2,4-bis-o-trimethylsilyl-5-fluorouracil. To obtain the final polymer-drug conjugate, the poly(phosphoester-urethane) [PPU-7] prepared according to the procedures of Example 7 (5 g) in methylene chloride (20 ml) was reacted with the 5-FU derivative in the presence of a stoichiometric amount of pyridine. After stirring for 18 hours at room temperature, 15 ml of methanol was added. After evaporation of the solvent, the residue was redissolved in dimethyl formamide and repeatedly precipitated into acetone, affording the desired polymer.

EXAMPLE 13

HYDROLYTIC STABILITY

Polymers derived from TDI (Examples 4–6; PPU-3, PPU-4, PPU-6) were subjected to an in vitro degradation test where the hydrolytic stability of each polymer was compared.

The degradation experiments were conducted in 0.1M phosphate buffer (pH 7.4). The polymers were compression molded into discs (1 cm × 1 mm), placed in 50 ml of pH 7.4 buffer, and incubated at 37° C. The release kinetics were followed by measuring the concentrations of the buffer solution by HPLC. The weight loss of the discs as a function of time was also recorded. The results are illustrated in FIG. 1.

A similar test was conducted with polymers derived from LDI (Examples 9–11; PLU-1, PLU-2, PLU-5). These polymers were placed in pH 7.4 phosphate buffer at 37° C. for 7 days and their weight losses recorded.

Figure 2:
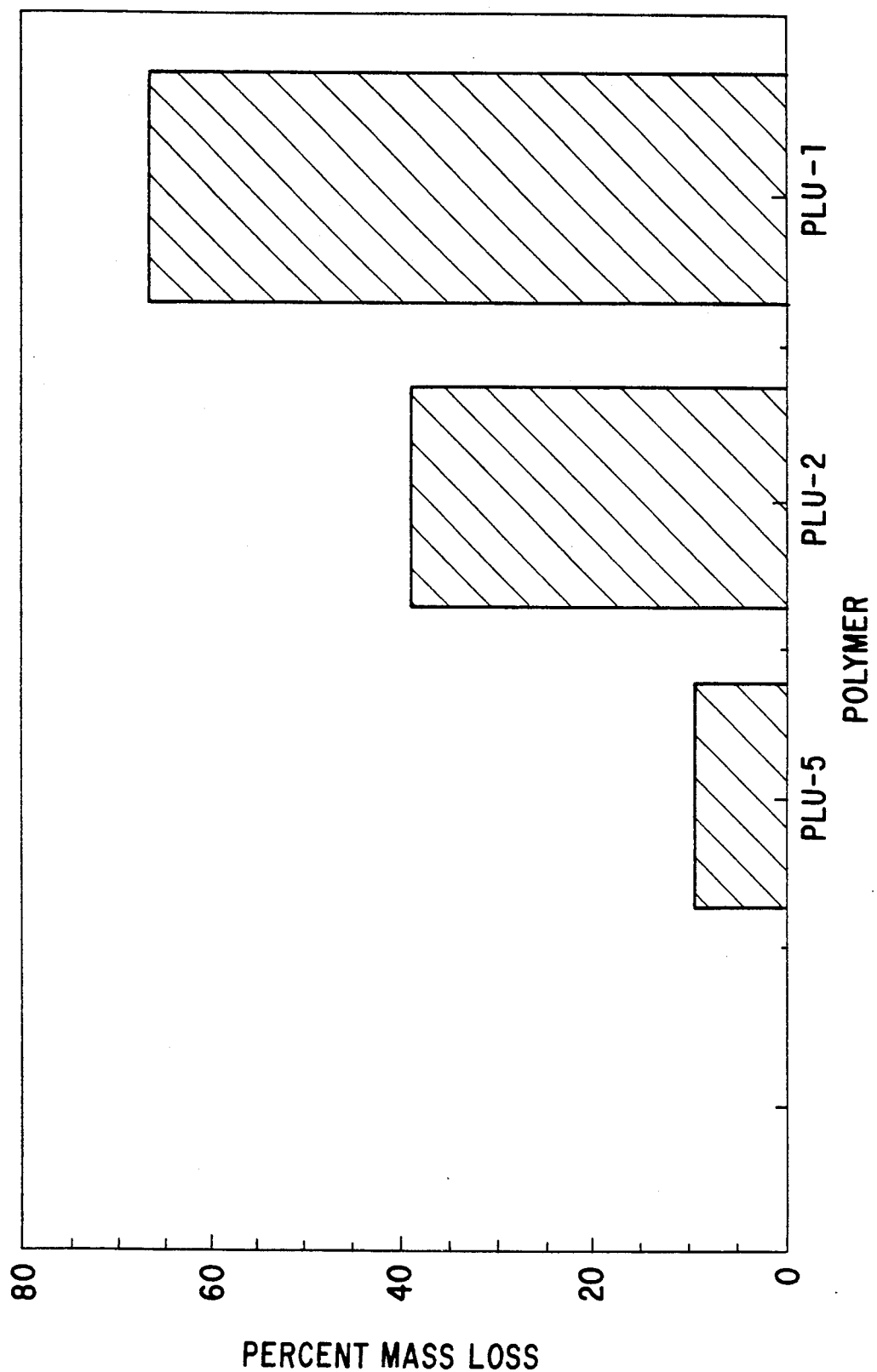
FIG. 2 compares the degradation (as expressed in terms of mass loss) of various poly(phosphoester-urethanes).

The results are shown in FIG. 2. Although all polymers experience substantial mass loss, PLU-1 (Example 9) undergoes degradation to a greater extent than the other two polymers. This is due to the presence of a polycaprolactone unit in the molecule, which is susceptible to hydrolysis.

EXAMPLE 14

IN VITRO DRUG RELEASE FROM NON-PENDANT POLYMERS

In a drug release experiment, an LDI based polyurethane prepared according to the procedure of Example 10 (PLU-2) was used.

Methotrexate was incorporated in the polymer by solvent casting from dimethylformamide. After removal of the solvent in a vacuum oven for about 48 hours, samples were punched out from a polymer sheet by a corkborer. Typically, a 10 w/w% drug loading was used.

Release experiments were conducted in a 0.1M pH 7.4 phosphate buffer containing 0.02 wt % of gentamicin sulfate to inhibit bacterial growth. The drug-loaded matrices were placed in 10 ml of buffer in 20 ml vials and incubated at 37° C. The release kinetics were followed by measuring the concentrations of the buffer solutions by UV spectroscopy. To approximate perfect sink conditions, the frequency of replacement of the buffer solutions was adjusted during the course of the release study to ensure that the drug concentration in buffer was below 20% of its saturation value.

Figure 3:
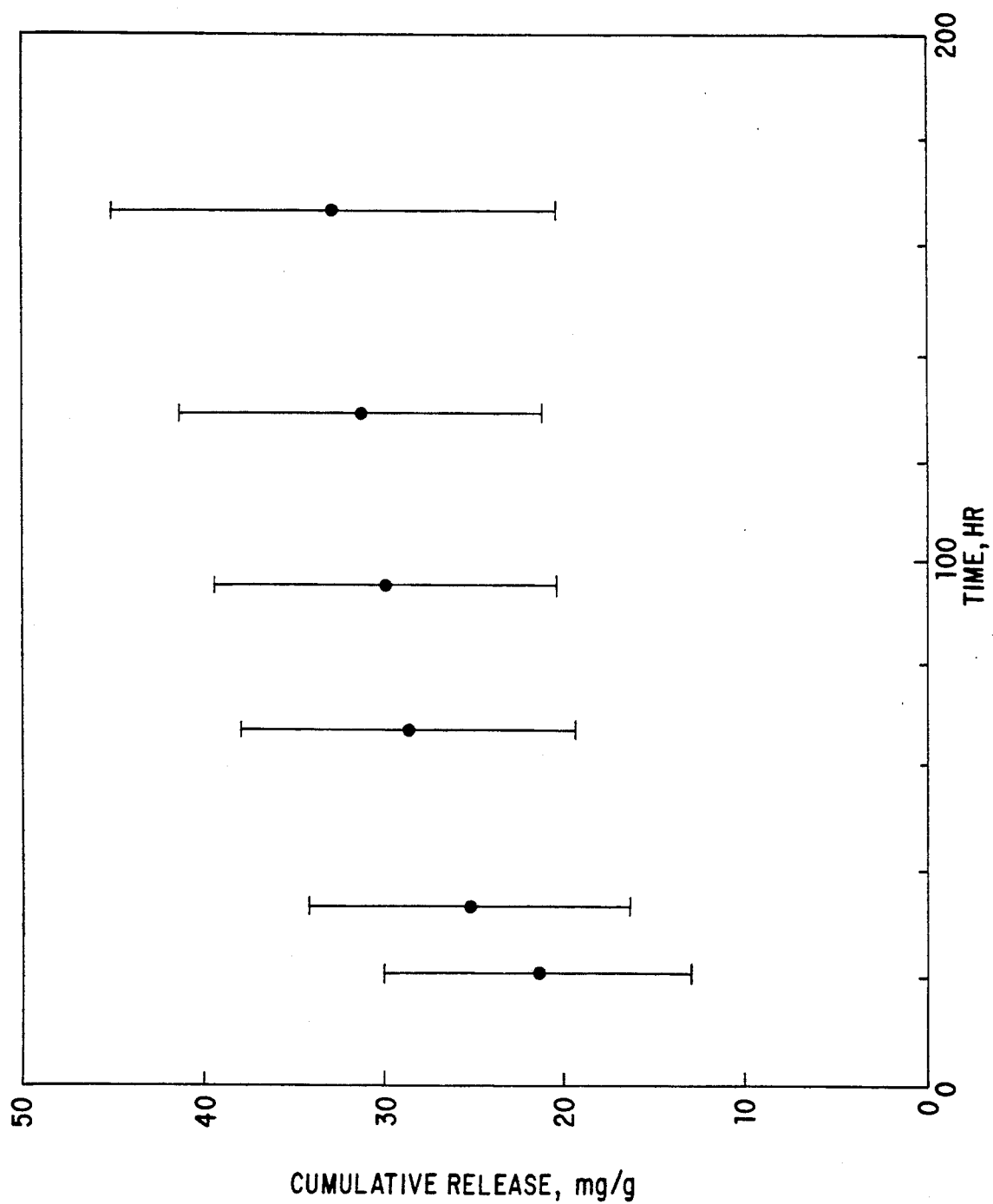
FIG. 3 shows the in vitro release of methotrexate when incorporated within the matrix of a poly(phosphoester-urethane) according to this invention.

The in vitro release of methotrexate from the polymer was thus determined as a function of time. The results of the test, as shown in FIG. 3, indicate that the release rate is diffusion-controlled.

EXAMPLE 15

IN VITRO DRUG RELEASE FROM PENDANT POLYMERS

In a drug release experiment, an MDI based polyurethane prepared according to the procedure of EXAMPLE 12 was used. The polymer incorporates 5-FU pendently bound to the polymeric matrix.

Figure 4:
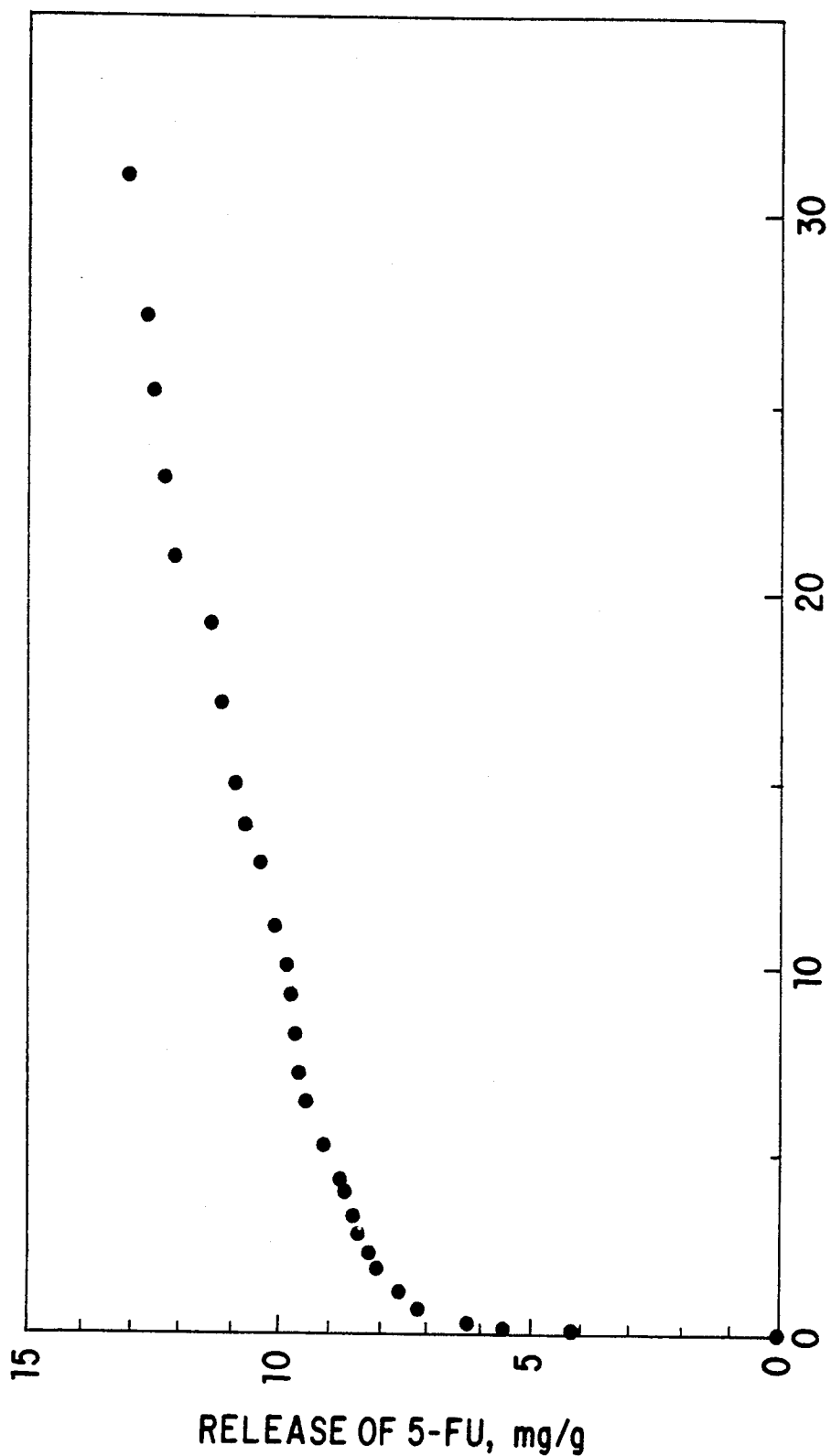
FIG. 4 shows the in vitro release of 5-fluorouracil when attached to the backbone matrix of a poly(phosphoester-urethane) according to this invention.

In in vitro release studies conducted under conditions similar to those described in EXAMPLE 14, a sustained release of 5-FU was observed for as long as 30 days and chemical integrity of the 5-FU was confirmed by HPLC. The results of the test are illustrated in FIG. 4.

PREPARATION 1

Bis(2-hydroxyethyl) phosphite

The title compound was synthesized by adapting the procedures of Barisov and Troev [*European Polym. J.* 9: 1077, 1973]. A molar ratio of 4:1 of ethylene glycol (73 ml; 1.3 mole) to diethylphosphite (43 ml; 0.22 mole) was placed in a round bottom flask equipped with a reflux condenser and a thermometer. A two ml fresh solution of sodium methoxide was added dropwise through a dropping funnel over a period of 2 minutes. The reaction mixture was kept at 135°–140° C. until the theoretical amount of ethanol was removed. The temperature was then raised to 152° C., while a vacuum of 20 mm Hg was applied for 3 hours to remove the unreacted ethylene glycol and impurities. The product obtained after work-up was a colorless viscous liquid.

PREPARATION 2

Ethyl 2,6-diisocyanatohexanoate

The procedures of Katsarava et al. [Dokl. Akad. Nauk USSR 281: 591, 1985] were modified and used.

L-lysine was converted to lysine ethyl ester by refluxing a mixture of 50 g of L-lysine monohydrochloride, 20 ml of thionyl chloride, and 300 ml of anhydrous ethanol. When the reaction mixture turned clear (after approximately 4 hours of reflux) excess ethanol was distilled off to yield the solid L-lysine ethyl ester. The L-lysine ester was then recrystallized in ethanol. Then, 25 g of L-lysine ethyl ester and 200 ml of 1,1,1,3,3,3-hexamethyldisilazane were placed in a round bottom flask with a condenser protected by a drying tube. While agitated, the suspension was maintained at 120° C. for 24 hours or more until the mixture turned clear. The excess 1,1,1,3,3,3-hexamethyldisilazane was removed and the crude product purified by vacuum distillation at 100° C. and 0.1 mmHg to yield a colorless liquid. Twenty five ml of the purified bis(trimethylsilyl)L-lysine was dissolved in 200 ml of anhydrous ethyl ether in the presence of 19.4 ml of triethylamine. While the mixture was cooled at −20° C., 15 g of triphosgene dissolved in 100 ml of anhydrous ethyl ether was added dropwise over a period of 30 minutes. The mixture was warmed to room temperature in 2 hours and let reacted for 40 hours. After the triethylamine hydrochloride was removed by filtration, the solution was evaporated to dryness. The residue was then purified by distillation at 120° C. and 0.1 mmHg. The typical yield of ethyl 2,6-diisocyanatohexanoate from L-lysine monohydrochloride was 50%.

The invention now being fully described, it will be apparent to one of ordinary skill in the art that many changes and modifications can be made without departing form the spirit or scope of the invention.

I claim:

1. A biocompatible and biodegradable poly-(phosphoester-urethane) of the formula:

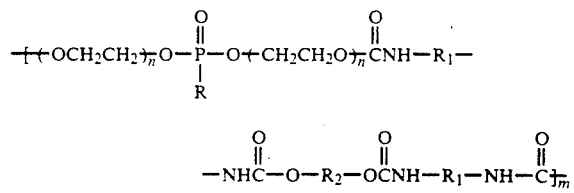

wherein R is hydrogen, alkyl having $C_1$–$C_{12}$, or a residue of a therapeutic agent capable of being released in a physiological environment;

$R_1$ is selected from the group consisting of $C_2$–$C_{20}$ alkylene, $C_6$–$C_{20}$ arylene, $C_7$–$C_{20}$ aralkylene, $C_6$–$C_{20}$ cycloalkylene, and a divalent residue of an amino acid, an amino acid derivative or an amino acid mimetic;

$R_2$ is selected from the group consisting of $C_2$–$C_6$ polyalkylene having a molecular weight of from about 500 to about 2000, $C_2$–$C_6$ polyalkenylene having a molecular weight of from about 500 to about 2000, $C_7$–$C_{20}$ aralkylene, $(R_3O)_l$ wherein $R_3$ is $C_2$–$C_6$ alkylene or acyl having from 2 to 6 carbons, and $l$ is an integer of from 5 to 30, and

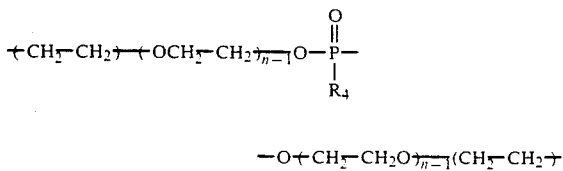

$-O(CH_2-CH_2O)_{\overline{m-1}}(CH_2-CH_2)-$ wherein $R_4$ is hydrogen or alkyl having $C_1-C_{12}$;
n is an integer of from 2 to 6; and
m is an integer of from about 10 to about $10^5$.

2. The poly-(phosphoester-urethane) according to claim 1, wherein $R_1$ is 4,4'-diphenylmethane, $R_2$ is $(R_3O)_l$ wherein $R_3$ is ethylene, l is 9, n is 2, and m is about $10^4$.

3. The poly-(phosphoester-urethane) according to claim 1, wherein $R_1$ is 2-methyl-1,3-phenylene, $R_2$ is selected from isopropylidene-1,4-biphenylene and $(R_3O)_l$ wherein $R_3$ is ethylene, l is 9, n is 2, and m is about $10^4$.

4. The poly-(phosphoester-urethane) according to claim 1, wherein $R_1$ is a residue of L-lysine.

5. The poly-(phosphoester-urethane) according to claim 4, wherein $R_1$ is 1-alkoxycarbonyl-1,5-pentylene, $R_2$ is 1,4-phenylene-dimethylene or $(R_3O)_l$ wherein $R_3$ is ethylene, l is 9, and n is 2.

6. The poly-(phosphoester-urethane) according to claim 5, wherein $R_1$ is ethoxycarbonyl-1,5-pentylene.

7. The poly-(phosphoester-urethane) according to any one of claims 1-6, wherein R is a therapeutic agent selected from the group consisting of a chemotherapeutic agent, a proteinous drug, a biological response modifier, a lectin, a radioisotope-labeled chemical, and a human or veterinary biological product.

8. The poly-(phosphoester-urethane) according to claim 7, wherein the therapeutic agent is 5-fluorouracil or a derivative thereof.

9. The poly-(phosphoester-urethane) according to claim 1, wherein R is hydrogen or alkyl having $C_1-C_6$.

* * * * *